(12) United States Patent
Yamada et al.

(10) Patent No.: US 10,677,770 B2
(45) Date of Patent: Jun. 9, 2020

(54) MOLECULAR DETECTION APPARATUS, MOLECULAR DETECTION METHOD, AND MOLECULAR DETECTOR

(71) Applicant: KABUSHIKI KAISHA TOSHIBA, Minato-ku (JP)

(72) Inventors: Ko Yamada, Yokohama (JP); Hirohisa Miyamoto, Kamakura (JP); Reiko Yoshimura, Kawasaki (JP); Norikazu Osada, Meguro (JP); Hiroko Nakamura, Yokohama (JP); Mitsuhiro Oki, Kawasaki (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 0 days.

(21) Appl. No.: 15/436,092

(22) Filed: Feb. 17, 2017

(65) Prior Publication Data

US 2018/0080911 A1    Mar. 22, 2018

(30) Foreign Application Priority Data

Sep. 20, 2016  (JP) .................. 2016-182746

(51) Int. Cl.
G01N 33/00 (2006.01)
G01N 27/414 (2006.01)
H01L 29/16 (2006.01)

(52) U.S. Cl.
CPC ..... *G01N 33/0037* (2013.01); *G01N 27/4141* (2013.01); *H01L 29/1606* (2013.01); *G01N 27/4146* (2013.01); *Y02A 50/245* (2018.01)

(58) Field of Classification Search
None
See application file for complete search history.

(56) References Cited

U.S. PATENT DOCUMENTS

| 9,297,785 B2 | 3/2016 | Amo et al. |
| 2008/0116490 A1 | 5/2008 | Stewart et al. |
| 2010/0033198 A1 | 2/2010 | Simonato et al. |

(Continued)

FOREIGN PATENT DOCUMENTS

| JP | 2008-216083 | 9/2008 |
| JP | 2010-19688 | 1/2010 |

(Continued)

OTHER PUBLICATIONS

Extended European Search Report dated Apr. 13, 2017 in Patent Application No. 17156678.9.

(Continued)

*Primary Examiner* — Xiaoyun R Xu
(74) *Attorney, Agent, or Firm* — Oblon, McClelland, Maier & Neustadt, L.L.P.

(57) ABSTRACT

A molecular detection apparatus 1 according to an embodiment includes: a collection unit collecting detection target gas containing molecules to be detected; a detector including a detection cell having an organic probe provided at a sensor unit, the organic probe capturing the collected molecule to be detected; and a discriminator discriminating the molecule to be detected by a detection signal generated by the molecule being captured by the organic probe. The detection cell has the organic probe containing a phosphonic acid structure or phosphoric acid structure.

7 Claims, 7 Drawing Sheets

(56) References Cited

U.S. PATENT DOCUMENTS

| | | | |
|---|---|---|---|
| 2010/0325073 A1 | 12/2010 | Haick | |
| 2011/0129937 A1 | 6/2011 | Naaman et al. | |
| 2012/0303288 A1 | 11/2012 | Morinaga | |
| 2013/0115705 A1 | 5/2013 | Patolsky et al. | |
| 2014/0220704 A1 | 8/2014 | Katz et al. | |
| 2015/0268208 A1 | 9/2015 | Rhodes et al. | |
| 2015/0362474 A1* | 12/2015 | Patolsky ............ | G01N 27/4146 436/110 |
| 2016/0209384 A1 | 7/2016 | Patolsky et al. | |

FOREIGN PATENT DOCUMENTS

| | | |
|---|---|---|
| JP | 2010-25719 | 2/2010 |
| JP | 2010-38569 | 2/2010 |
| JP | 2010-38840 | 2/2010 |
| JP | 2010-44065 | 2/2010 |
| JP | 2010-71906 | 4/2010 |
| JP | 2010-139269 | 6/2010 |
| JP | 2011-80798 | 4/2011 |
| JP | 2012-247189 | 12/2012 |
| JP | 2012-247198 | 12/2012 |
| JP | 2013-529308 | 7/2013 |
| JP | 2014-505580 | 3/2014 |
| WO | WO 2012/061607 A2 | 5/2012 |
| WO | WO 2015/0012186 A1 | 1/2015 |
| WO | WO 2016/0031080 A1 | 3/2016 |

OTHER PUBLICATIONS

Beibei Zhan, et al., "Graphene Field-Effect Transistor and Its Application for Electronic Sensing" Small, XP055200050, Jul. 4, 2014, pp. 1-24 with cover pages.

Jingquan Liu, et al., "Strategies for chemical modification of graphene and applications of chemically modified graphene" Journal of Materials Chemistry, XP055359350, vol. 22, No. 25, Apr. 2, 2012, pp. 12435-12452.

* cited by examiner

[ORGANIC COMPOUND 1A]   [ORGANIC COMPOUND 1B]   [ORGANIC COMPOUND 1C]

FIG. 9
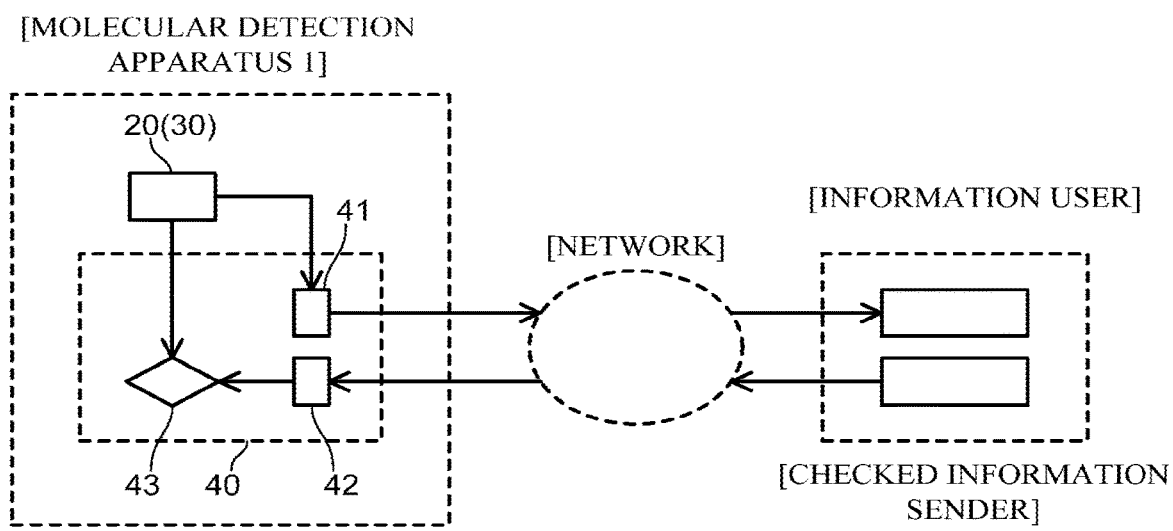
FIG. 10
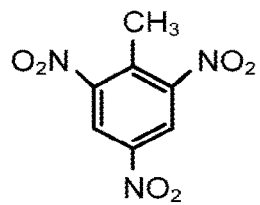
[MOLECULE TO BE
DETECTED 1]
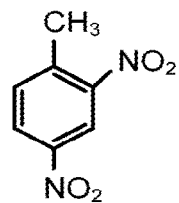
[MOLECULE TO BE
DETECTED 2]
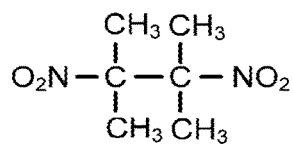
[MOLECULE TO BE
DETECTED 3]

MOLECULAR DETECTION APPARATUS, MOLECULAR DETECTION METHOD, AND MOLECULAR DETECTOR

CROSS-REFERENCE TO RELATED APPLICATION

This application is based upon and claims the benefit of priority from Japanese Patent Application No. 2016-182746 filed on Sep. 20, 2016; the entire contents of which are incorporated herein by reference.

FIELD

Embodiments described herein generally relate to a molecular detection apparatus, a molecular detection method, and a molecular detector.

BACKGROUND

A water heater or the like for household use is provided with an equipment that detects carbon monoxide generated when incomplete combustion occurs and notifies the risk thereof at an early stage. Such a gas component considerably affects a human body. According to the guidelines from LP gas safety committee, it is set that a carbon monoxide concentration of approximately 200 ppm (parts per million) causes headaches. Although various methods have been known as a method of detecting a gas component having a relatively higher concentration, the detection methods have been limited for detecting the gas component having a concentration of ppb (parts per billion) to ppt (parts per trillion), which corresponds to an extremely low concentration.

At a disaster site or a site at which an act of terrorism occurs or the like, it has been desired to sense the risk in advance by detecting an extremely small amount of the gas component. The gas component having an extremely low concentration is often detected by use of a large equipment in research facilities. In this case, a large sized installation type equipment, which is expensive and has large weight and volume, such as a gas chromatography or a mass spectrometer is required. Under such circumstances, it has been required to provide an apparatus that is capable of detecting the gas component having an extremely low concentration in real time, in other words, an apparatus that has a smaller weight and volume and a better portability and enables selective and higher sensitive detection of the gas component having an extremely low concentration in the order of ppt to ppb.

By the way, examples of the gas component required to be detected at an extremely low concentration include sarin, an organophosphorus compound contained in toxic agricultural chemicals, and toxic gas components such as nitrogen mustard gas and sulfur mustard gas. Besides, components of an explosive nitro compound and the like are also required to be detected at an extremely low concentration. For example, detonating explosives release an extremely small amount of volatile component even in a sealed state, and it is considered that a capability of detecting such a gas component at an extremely small concentration brings about a deterrent effect of an act of terrorism. Conventionally, it is general that a volatile component of the nitro compound or the like at a site such as an airport is detected by a trained police dog or the like. Such a gas component detection method is very effective in terms of a deterrent to an act of terrorism, but such an approach by use of an animal is high in cost and further has a difficulty in securing accuracy in a normal state.

As a detection element for the gas component having a low concentration, for example, an element has been known that has a conductive layer in which a surface of a carbon nanostructure is surface modified with an organic substance or the like that selectively reacts with or adsorbs a specific substance and measures a potential difference or the like that changes depending on the gas component that has adhered to the surface of the carbon nanostructure. In such a detection element, types of the organic substance themselves that functions as a detection probe are limited, and thus an organic substance capable of sufficiently interacting with the volatile component of the nitro compound has not been found out. In the meantime, there has been proposed a method of detecting the presence or amount of nitro compound component by providing, on a nanostructure such as a nanowire or a nanotube, a functionality component having an electron releasing group, such as amine, that bonds to the nitro compound component to form a charge transfer complex. In this method, the formation of charge transfer complex by the electron releasing group on a sensor side and the nitro compound component is likely to be affected by environmental conditions with the presence of the nitro compound component. Therefore, there is a problem that detection accuracy of the nitro compound component decreases depending on the environmental condition.

BRIEF DESCRIPTION OF THE DRAWINGS

FIG. 9 is a view illustrating an information processing unit in the molecular detection apparatus according to the embodiment.

FIG. 10 is a view illustrating examples of a molecule to be detected that is detected in the molecular detection apparatus according to the embodiment.

DETAILED DESCRIPTION

According to an embodiment, a molecular detection apparatus is provided. A molecular detection apparatus includes: a collection unit collecting detection target gas containing molecules to be detected; a detector including a detection cell having a sensor unit and an organic probe disposed at the sensor unit, the organic probe containing a phosphonic acid structure or phosphoric acid structure and capturing the molecule collected in the collection unit; and a discriminator discriminating the molecule to be detected by a detection signal generated from the sensor unit by the molecule being captured by the organic probe in the detection cell.

Hereinafter, there will be explained a molecular detection apparatus, a molecular detection method, and a molecular detector according to embodiments with reference to the drawings. In each embodiment, substantially the same constituent elements are denoted by the same reference signs and an explanation thereof will be omitted in some cases. The drawings are schematic, and a relation of the thickness and the planar dimension of each unit, a thickness ratio of each unit, and so on may differ from actual ones.

Figure 1:
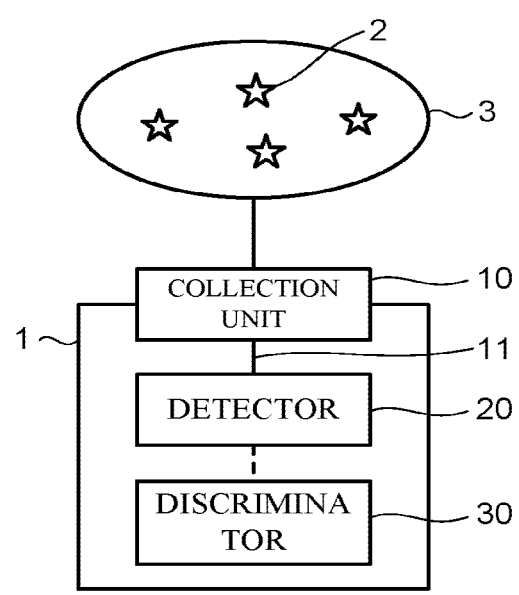
FIG. 1 is a block diagram illustrating a molecular detection apparatus according to an embodiment.

FIG. 1 is a block diagram illustrating a molecular detection apparatus according to the embodiment. A molecular detection apparatus 1 illustrated in FIG. 1 is, for example, an apparatus that detects, from detection target gas 3 containing molecules to be detected (substances to be detected) 2 generated from a gas generation source, the molecule to be detected 2, and includes a collection unit 10, a detector (molecular detector) 20, and a discriminator 30. The detection target gas 3 containing the molecules to be detected 2 is, first collected by the collection unit 10 in the molecular detection apparatus 1. The collection unit 10 has a collection port for the detection target gas 3 and is connected to the detector 20 via a gas flow channel 11. The collection unit 10 may include a filter for removing impurities such as fine particles contained in the detection target gas 3.

Figure 2:
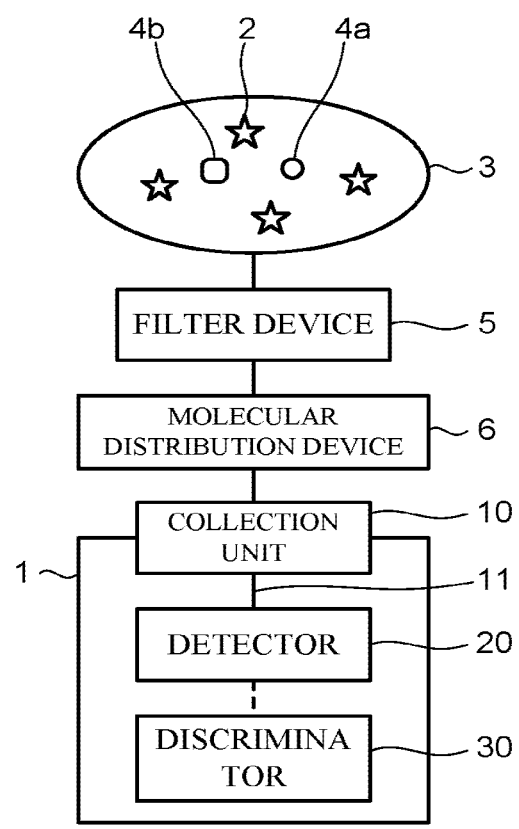
FIG. 2 is a block diagram illustrating a modified example of the molecular detection apparatus illustrated in FIG. 1.

The detection target gas 3 sometimes contains, as an impurity, substances having a molecular weight, a molecular structure or the like similar to that of the molecule to be detected 2. Further, as illustrated in FIG. 2, the molecules to be detected 2 drifting in the air often exist in a state where the molecules to be detected 2 are mixed with various foreign substances 4 (4a and 4b) such as an odor component and a fine particle. From those perspectives, as illustrated in FIG. 2, the detection target gas 3 may be sent to the molecular detection apparatus 1 after being preprocessed by a filter device 5, a molecular distribution device 6, and the like beforehand.

For the filter device 5 out of the devices of preprocess, a generally-used moderate-to-high performance filter or the like is used. The filter device 5 removes particulate substances such as fine particles contained in the detection target gas 3. The detection target gas 3, from which the particulate substances are removed in the filter device 5, is then sent to the molecular distribution device 6. As the molecular distribution device 6, there can be cited an apparatus that ionizes the detection target gas 3 to form an ionized substance group, applies voltage to the ionized substance group to allow the ionized substance group to fly at a speed proportional to the mass thereof, and separates an ionized substance of the molecule to be detected 2 from the ionized substance group using a flight speed based on the difference in mass among ionized substances and a time of flight based on the flight speed. As the molecular distribution device 6 as above, a device including an ionization unit, a voltage application unit, and a time-of-flight separation unit is used.

Figure 3:
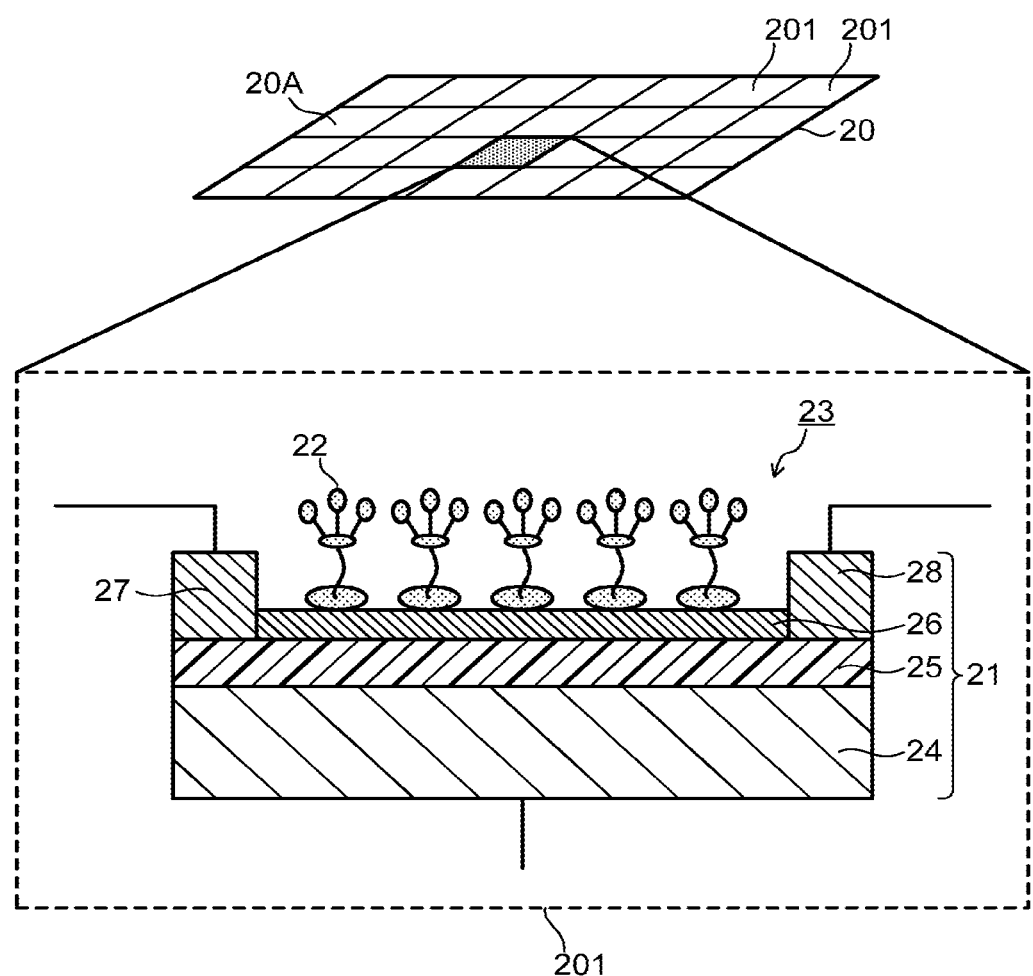
FIG. 3 is a view illustrating a configuration of a detector according to the embodiment.

The detection target gas 3 containing the molecules to be detected 2 is collected by the collection unit 10 directly, or is collected by the collection unit 10 after being preprocessed by the devices such as the filter device 5 and the molecular distribution device 6. The molecules to be detected 2 collected by the collection unit 10 are then sent to the detector 20 thorough the gas flow channel 11. The detector 20, as illustrated in FIG. 3, includes a detection surface 20A sectioned into a plurality of detection cells 201.

The detection surface 20A of the detector 20 is disposed towards an output port (not illustrated), for the molecules to be detected 2, of the gas flow channel 11. The plural detection cells 201 each include a detection element 23 having a sensor unit 21 and organic probes 22 provided at the sensor unit 21. FIG. 3 illustrates the detection element 23 using a graphene field effect transistor (GFET) for the sensor unit 21.

The GFET serving as the sensor unit 21 includes a semiconductor substrate 24 that functions as a gate electrode, an insulating film 25 disposed as a gate insulating layer on the semiconductor substrate 24, a graphene layer 26 disposed as a channel on the insulating film 25, a source electrode 27 provided at one end of the graphene layer 26, and a drain electrode 28 provided at the other end of the graphene layer 26. The organic probes 22 are disposed on the graphene layer 26. The molecules to be detected 2 that are led into the detector 20 are captured by the organic probes 22 on the graphene layer 26. Electrons are moved from the molecules to be detected 2 captured by the organic probes 22 to the GFET 21, thereby performing electric detection. In this way, the intended molecule to be detected 2 is detected.

An organic substance forming the organic probe 22 has a property of dissolving in a solvent. Thus, by applying a solution obtained by dissolving the organic substance in a solvent on the graphene layer 26, the organic probe 22 can be installed at the graphene layer 26. In order to easily obtain an interaction with the graphene, the organic probe 22 preferably has a portion having such a structure as a pyrene ring. A molecule having such a structure as the pyrene ring interacts with a hexagonally shaped π electron system formed by carbon of the graphene, and forms an interaction state of what is called π-π stacking. Low-concentration probe molecules are dissolved in a solvent and the resultant is applied to the graphene, and thereby the π-π stacking is formed between the pyrene ring and the graphene and the probe molecules are aligned on the graphene to be fixed. By using such a self-alignment action, the organic probe 22 can be installed on the graphene layer 26. The organic compound forming the organic probe 22 will be described in detail later.

When the molecules to be detected 2 are captured by the organic probes 22 provided on the graphene layer 26, an output from the GFET 21 changes. The case of a single layer of graphene means that there is zero gap, and thus, the source electrode 27 and the drain electrode 28 are continuously electrified normally. When the number of graphene layers increases to two or three layers, a band gap is generated, but such a band gap in an actual system is relatively smaller than that considered from a strict theoretical value. When the gate insulating layer 25 has a dielectric constant approximately similar to that of a silicon dioxide film, the source electrode 27 and the drain electrode 28 are often continuously electrified. Thus, the graphene layer 26 may be formed of a stack composed of about five graphene layers or less as well as the single layer structure of graphene.

The molecule to be detected 2 flying in the vicinity of the organic probe 22 is attracted to the organic probe 22 by hydrogen bonding force or the like, or comes into contact with the organic probe 22 in some cases. When the contact with the molecule to be detected 2 occurs, an interchange of electrons occurs with the organic probe 22 and the organic probe 22 transmits an electrical change to the graphene layer 26 being in contact therewith. The electrical change transmitted from the organic probe 22 to the graphene layer 26 disturbs the flow of electricity between the source electrode 27 and the drain electrode 28, and thus the GFET 21 functions as a sensor.

Figure 4:
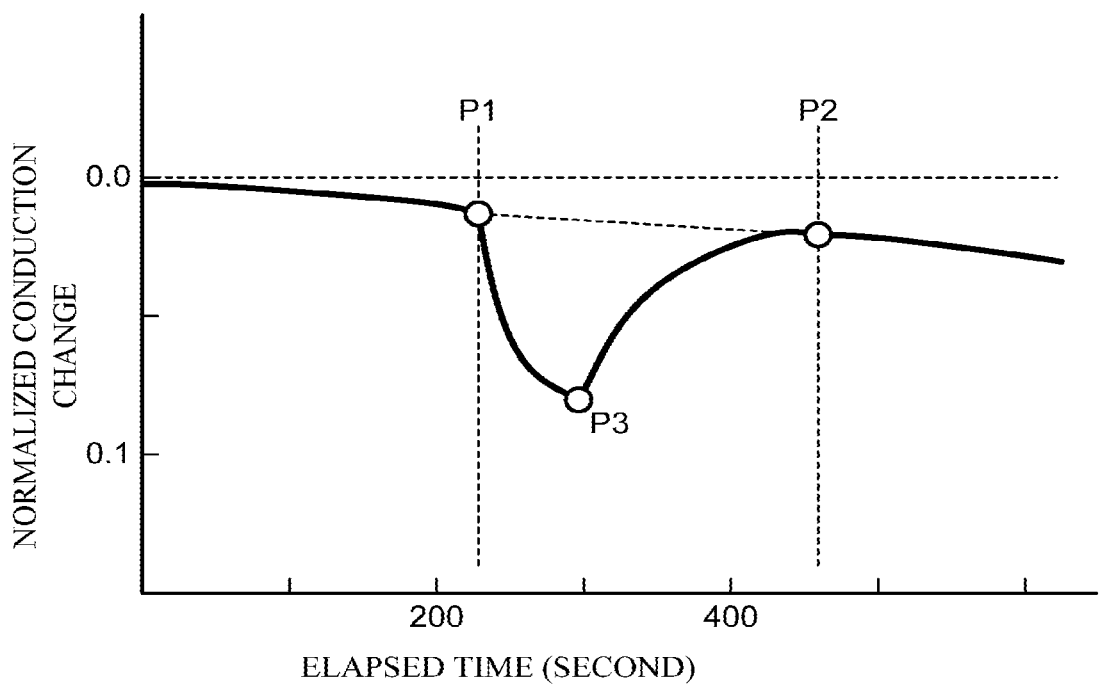
FIG. 4 is a view illustrating one example of a detected waveform of a molecule to be detected by the molecular detection apparatus according to the embodiment.

With the GFET 21 using the graphene layer 26 as a channel, even an extremely slight electrical change appears significantly as an output. As a result, it is possible to constitute the highly sensitive detection element 23. The sensor using the GFET 21 also has a tendency that electric current flows between the source electrode 27 and the drain electrode 28 without application of voltage to the gate electrode 24 because the graphene has a property as a zero-gap semiconductor. Thus, the GFET 21 functions as a sensor as it is. However, normally, in the GFET 21 electric current is applied between the source electrode 27 and the drain electrode 28 in a state of applying voltage to the gate electrode 24, and an electrical change of the gate electrode 24 is observed when the organic probe 22 captures the molecule to be detected 2. FIG. 4 illustrates one example of a detected waveform of the molecule to be detected 2 by the molecular detection apparatus 1. When the organic probe 22 captures the molecule to be detected 2, such a change as illustrated in FIG. 4 appears in the detected waveform. A method of converting a detected waveform into a signal intensity can be variously considered. For example, a value calculated from an area defined by P1, P2 and P3 being a point of a peak in FIG. 4 is set as the intensity. However, the conversion is not necessarily limited to this method.

In the detection of the molecule to be detected 2 performed by the above-described detection element 23, as the movement of electrons from the molecule to be detected 2 that is captured by the organic probe 22 to the GFETT 21 is higher, the function as the sensor is further increased. The sensor using the GFET 21 is regarded as the most sensitive FET sensor, and can improve sensitivity about three times as compared to a sensor using a carbon nanotube. Thus, using the detection element 23 in which the GFET 21 and the organic probe 22 are combined enables higher sensitive detection of the molecule to be detected 2.

Figure 5:
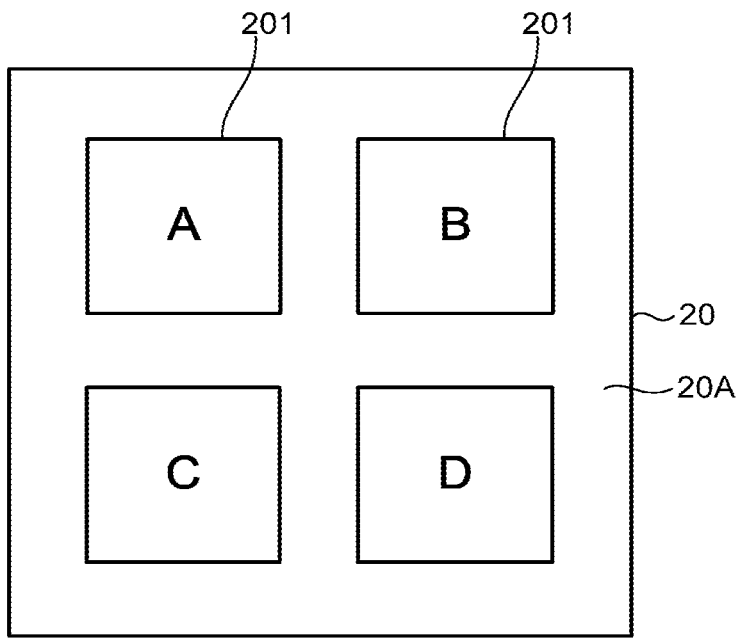
FIG. 5 is a view illustrating one example of a plurality of detection cells in the molecular detection apparatus according to the embodiment.

FIG. 5 illustrates the detection surface 20A on which the plural detection cells 201 are arranged in a grid pattern (an array pattern), but is not necessarily limited thereto. The plural detection cells 201 may be arranged linearly. At least some of the organic probes 22 provided at the graphene layers 26 of the plural detection cells 201 are different in working strength (bond strength) with the molecule to be detected 2. That is, the plural detection cells 201 include a plurality of the organic probes 22 different in the bond strength with the molecule to be detected 2. All the organic probes 22 may be different in the bond strength with the molecule to be detected 2, or some of the organic probes 22 may be different in the bond strength with the molecule to be detected 2.

Figure 6:
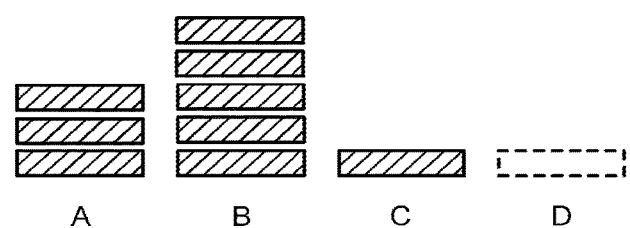
FIG. 6 is a view illustrating one example of detection results of a molecule to be detected by a plurality of the detection cells illustrated in FIG. 5.

FIG. 5 illustrates a grid-shaped sensor in which the detection surface 20A of the detector 20 is sectioned into four detection cells 201, namely a detection cell A, a detection cell B, a detection cell C, and a detection cell D. At least in some of the detection cells A to D, different types of the organic probes 22, namely the plural organic probes 22 different in the bond strength with the molecule to be detected 2, are provided. The plural organic probes 22 each have an interaction with the molecule to be detected 2, but are different in the bond strength with the molecule to be detected 2, and thus detection signals different in intensity are output. FIG. 6 illustrates one example of detection signals by the detection cells A to D. The detection signals from the detection cells A to D are different in signal intensity respectively due to the bond strength of the organic probe 22 with the molecule to be detected 2.

The signals detected in the detection cells A to D are sent to the discriminator 30 to be signal-processed. The discriminator 30 converts the detection signals from the detection cells A to D into intensities and analyzes signal patterns based on intensity differences of these detection signals (for example, four detection signal patterns illustrated in FIG. 6). The discriminator 30 stores therein signal patterns according to a substance to be detected and compares these signal patterns and the signal patterns detected in the detection cells A to D, to thereby discriminate the molecule 2 detected in the detector 20. Such a signal process is called a pattern recognition method here. The pattern recognition method enables detection and discrimination of the molecule to be detected 2 by signal patterns peculiar to the substance to be detected like a dactyloscopy, for example. Accordingly, selective and higher sensitive detection of a gas component having an extremely low concentration in the order of ppt to ppb (the molecule to be detected 2) is enabled.

Application of the above-described pattern recognition method enables selective and higher sensitive detection and discrimination of the molecule to be detected 2 even when impurities are mixed in the detection target gas 3 that is led to the detector 20. For example, in the case when the molecule to be detected 2 is dimethyl methylphosphonate (DMMP, molecule weight: 124), which is a typical material for a toxic organophosphorus compound, there exist agricultural chemicals containing phosphoric acid such as dichlorvos having a similar chemical structure and organophosphorous pesticides, which are used often, such as malathion, chlorpyrifos, and diazinon. In order to prevent an erroneous detection of these substances, discrimination by such signal patterns as illustrated in FIG. 6 is effective. In other words, since the signal patterns detected in the detection cells A to D are different due to the above-described respective substances, application of the pattern recognition method enables selective and higher sensitive detection of the detection target substance even when an impurity that has a similar molecular weight and a similar constituent element is mixed.

Figure 7:
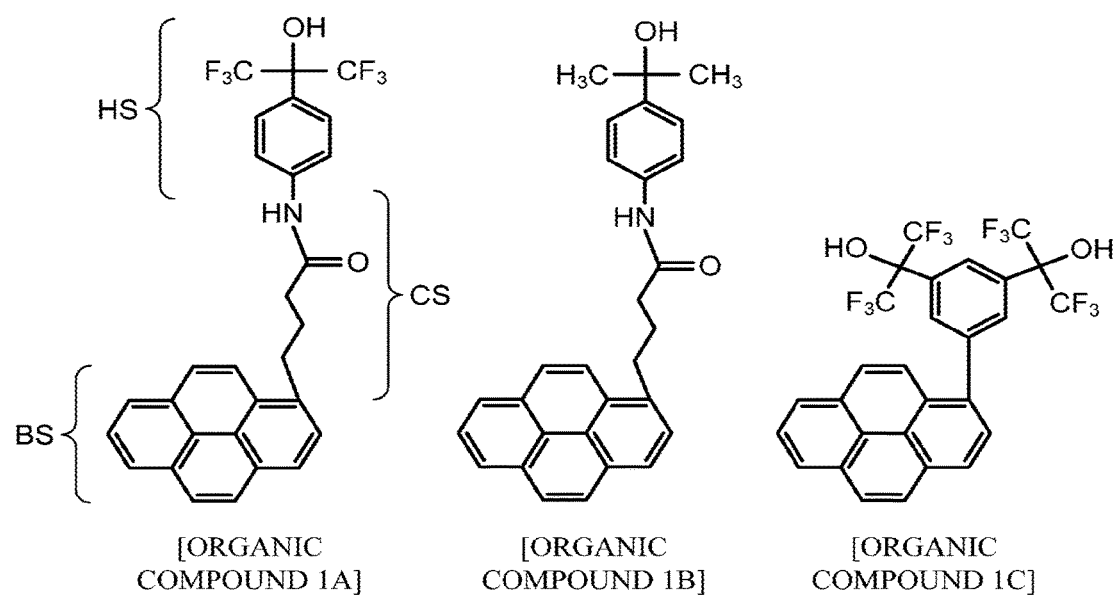
FIG. 7 is a view illustrating a first example of organic compounds used for organic probes in the embodiment.

Next, there is described in detail the organic probe 22 to be used for the detection cell 201 of the molecular detection apparatus 1 according to the embodiment. An organic compound forming the organic probe 22 has, for example a hydroxy group (—OH) as a reactive group with respect to the molecule to be detected 2. However, only the reactive group hardly reacts with the gas component. Thus, for the purpose of enhancing a hydrogen bonding property or the like, an organic compound having a structure with a fluorinated group around the reactive group (—OH) is preferably applied. Typical examples of such an organic compound forming the organic probe 22 are illustrated in FIG. 7. In order to have a fluorinated group around the reactive group (—OH), for example, a fluorinated alkyl group such as a trifluoromethyl group (—CF$_3$) or a hexafluoroethyl group (—C$_2$F$_5$) is, as a neighboring group, introduced into carbon to which the reactive group (—OH) is bonded. As a structure having such a substituted alkyl group, a 1,1,1,3,3,3-hexafluoro-2-phenyl-2-propanol structure, an α-trifluoromethylbenzyl structure, and so on, which are illustrated in FIG. 7, can be cited. These structures have an effect of enhancing activity of the reactive group (OH group) with fluorine having a high electronegativity. The reactive group is not limited to the hydroxy group (—OH), and may be an amino group (—NH$_2$) or the like. Further, the neighboring group may be an alkyl group such as a methyl group (—CH$_3$) or an ethyl group (—C$_2$H$_5$).

The organic compound forming the organic probe 22 is, as illustrated in an organic compound 1A in FIG. 7, preferably be comprised of an organic compound that has a head portion HS having the above-described reactive group and neighboring group, a base portion BS serving as an installation portion for the graphene layer 26 or the like, and a connecting portion CS connecting the head portion HS and the base portion BS. The head portion HS is preferred to be an aromatic hydrocarbon group having the reactive group and the neighboring group. The base portion BS is preferred to be a substituted or unsubstituted polycyclic aromatic hydrocarbon group having a polycyclic structure such as a pyrene ring, an anthracene ring, a naphthacene ring, or a phenanthrene ring, and further preferred to be a substituted or unsubstituted pyrene group. The connecting portion CS is a single bond or an organic group. It may be an alkylene group such as a methylene group or an ethylene group, but is preferred to be an organic group having a characteristic group such as an ether bond (—O—), an ester bond (—C(=O)O—), a carbonyl bond (—CO—), an amide bond (—NH—CO—), or an imide bond (—CO—NH—CO—).

The organic probes 22 comprised of the above-described organic compounds (for example, the organic compounds illustrated in FIG. 7) function effectively for the dimethyl methylphosphonate (DMMP) or the like, which is a typical material for a toxic organophosphorus compound, to thus be able to detect the molecule to be detected 2 comprised such compound molecules with higher sensitivity. In the meantime, the organic compounds described above have limited effectiveness against an explosive nitro compound, which is, for example, a nitro compound such as trinitrotoluene (C$_6$H$_2$(CH$_3$)(NO$_2$)$_3$/TNT) or picric acid (C$_6$H$_2$(OH)(NO$_2$)$_3$), and the organic probes 22 does not function effectively. The organophosphorus compound has a characteristic bond with phosphorus (P) and oxygen (O), while the nitro compound typified by TNT has high molecular structure symmetry and has small intramolecular polar deviation. In order to capture such a substance by the organic probe 22, it is necessary to devise the structure of an organic compound.

In the molecular detection apparatus 1 according to the embodiment, the organic probe 22 having an interaction with a nitro compound comprises an organic compound having a phosphonic acid structure or phosphoric acid structure. The phosphonic acid structure or the phosphoric acid structure has a double bond (P=O) of phosphorus and oxygen with relatively large polarity at a portion adjacent to the hydroxy group (—OH) as the reactive group and also has large intramolecular deviation, and thus exhibits a good interaction with the nitro compound that has high molecular structure symmetry and has small intramolecular polar deviation. The organic compound having a phosphonic acid structure or phosphoric acid structure is provided at the sensor unit 21 in the detection cell 201 as the organic probe 22, thereby making it possible to increase a property of capturing the nitro compound molecule. Therefore, it becomes possible to improve detection sensitivity and detection accuracy of the detector 20 for the nitro compound molecules. Further, the organic probe 22 having a phosphonic acid structure or phosphoric acid structure attracts the nitro compound molecule due to intramolecular electrical deviation or the like to then capture it, so that higher sensitive detection of the nitro compound molecule is enabled without being affected by peripheral environmental conditions or the like. That is, it is possible to increase the detection accuracy for the nitro compound molecules.

Figure 8:
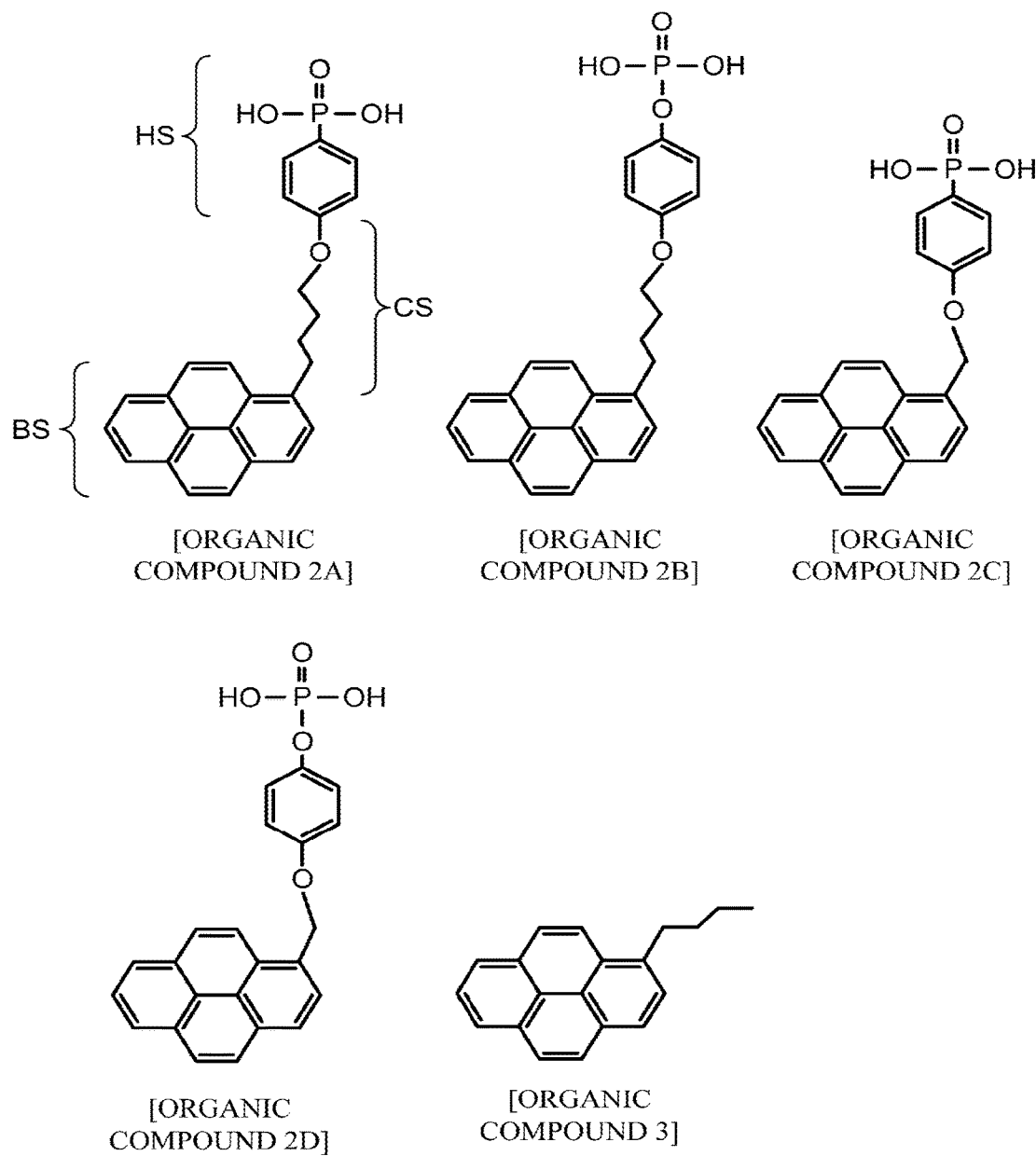
FIG. 8 is a view illustrating a second example of organic compounds used for the organic probes in the embodiment.

FIG. 8 illustrates examples of the organic compound having a phosphonic acid structure or phosphoric acid structure. Organic compounds 2A and 2C have a phosphonic acid structure, and organic compounds 2B and 2D have a phosphoric acid structure. These organic compounds 2A to 2D, similarly to the above-described organic compounds 1A to 1C, each have a head portion HS containing a phosphonate group (H$_2$PO$_3$—) or a phosphate group (H$_2$PO$_4$—) having a hydroxy group (—OH) as the reactive group, a base portion BS serving as an installation portion for the graphene layer 26 or the like, and a connecting portion CS connecting the head portion HS and the base portion BS. The head portion HS is preferred to be an aromatic hydrocarbon group having a phosphonate group or phosphate group, and further preferred to be a phenyl group having a phosphonate group or phosphate group. The aromatic hydrocarbon group containing a phenyl group may have a substituent other than the phosphonate group or the phosphate group.

The base portion BS is, similarly to the above-described organic compounds 1A to 1C, preferred to be a substituted or unsubstituted polycyclic aromatic hydrocarbon group having a polycyclic structure such as a pyrene ring, an anthracene ring, a naphthacene ring, or a phenanthrene ring, and further preferred to be a substituted or unsubstituted pyrene group. The connecting portion CS is a single bond or an organic group. It may be an alkylene group such as a methylene group or an ethylene group, but is preferred to be a characteristic group such as an ether bond (—O—), an ester bond (—C(=O)O—), a carbonyl bond (—CO—), an amide bond (—NH—CO—), or an imide bond (—CO—NH—CO—), or an organic groups such as an allkylene groups having the above-described characteristic group. The organic compounds 2A and 2B each have a [—C$_4$H$_8$O—] group as the connecting portion CS, and the organic compounds 2C and 2D each have a [—CH$_2$O] group as the connecting portion CS.

As for the above-described organic compounds having a phosphonic acid structure or phosphoric acid structure, based on the structural difference of a functional group having the reactive group (—OH) in the head portion HS (the phosphonate group or phosphate group), the difference in carbon number of a bivalent hydrocarbon group as the connecting portion CS, and the like, bond strengths of the organic probes 22 comprised of the organic compounds with the nitro compound molecule as the molecule to be detected 2 vary. Thus, the organic probes 22 comprised of such organic compounds different in the bond strength with the nitro compound molecule are provided at each of the four detection cells A to D in the detector 20 illustrated in FIG. 5, for example, and thereby intensities of the detection signals when the organic probes 22 capture the nitro compound molecule can be made to differ. Accordingly, such signal patterns based on the intensity differences of the detection signals as illustrated in FIG. 6 can be obtained, thereby enabling detection and discrimination of the nitro compound molecule.

The organic compounds forming the organic probes 22 provided in the plural detection cells 201 are not limited only to the organic compounds having a phosphonic acid structure or phosphoric acid structure. The organic probe 22 comprised of the organic compound having a phosphonic acid structure or phosphoric acid structure only needs to be provided in at least one of the plural detection cells 201. The other detection cells 201 may have the organic probes 22 comprised of the organic compounds illustrated in FIG. 7 and the organic probe 22 comprised of the organic compound 3 illustrated in FIG. 8. The organic compound 3 illustrated in FIG. 8 does not have a reactive group, and thus the detection cell 201 using the organic compound 3 can be used as a standard cell indicating a reference. Further, the detection of the nitro compound molecule as the molecule to be detected 2 is not limited to the pattern recognition method using the plural detection cells 201. For example, it is also possible to configure so that the organic probe 22 having a phosphonic acid structure or phosphoric acid structure is provided in the single detection cell 201 and by the detection signal generated by the organic probe 22 capturing the nitro compound molecule, the molecule to be detected 2 is discriminated.

The detector 20 using the organic probe 22 having a phosphonic acid structure or phosphoric acid structure works effectively when detecting the nitro compound molecule as the molecule to be detected 2 as described above. Examples of the nitro compound as the molecule to be detected 2 include aromatic nitro compounds such as trinitrotoluene ($C_6H_2(CH_3)(NO_2)_3$), picric acid ($C_6H_2(OH)(NO_2)_3$), and dinitrotoluene ($C_6H_3(CH_3)(NO_2)_2$), an aliphatic nitro compound such as 2,3-dimethyl-2,3-dinitrobutane, and so on. The detector 20 using the organic probe 22 having a phosphonic acid structure or phosphoric acid structure is not limited to the detection of the nitro compound molecules, and can be used also for detection of other gas molecules.

According to the molecular detection apparatus 1 of the embodiment, for example, application of the pattern recognition method enables selective and higher sensitive detection of a gas molecule having an extremely low concentration in the order of ppt to ppb. Further, using the organic probe 22 having a phosphonic acid structure or phosphoric acid structure enables higher sensitive detection of a nitro compound molecule that has high molecular structural symmetry and small intramolecular polarity deviation without being affected by environmental conditions with the presence of the molecule to be detected 2 or the like. Accordingly, higher sensitive detection of a gas molecule such as the nitro compound molecule is enabled. Further, the detector 20 and the discriminator 30 increase the detection sensitivity and the detection accuracy, thereby enabling miniaturization of the molecular detection apparatus 1. Accordingly, it becomes possible to provide the molecular detection apparatus 1 with portability and detection accuracy both achieved. Such a molecular detection apparatus 1 effectively fulfills its function at various field sites such as a disaster site or a site of an act of terrorism.

Results of detection and discrimination results of the molecule to be detected 2 obtained by the molecular detection apparatus 1 according to the embodiment may be transmitted over information networks to be utilized. FIG. 9 illustrates a configuration example of the molecular detection apparatus 1 with an information processing unit 40 attached thereto or provided internally, the information processing unit 40 including a function of transmitting detection information of the molecule to be detected 2 over an information network and a function of checking the detection information and reference information obtained from the information network. The information processing unit 40 includes an information transmitting unit 41 transmitting detection information of the molecule to be detected 2, an information receiving unit 42 receiving reference information, and an information checking unit 43 checking the detection information and the reference information. The information processing unit 40 may have only one of an information transmitting function and an information checking function including an information receiving function.

The information transmitting unit 41 transmits the detection information of the molecule to be detected 2 to an information user over the network. In order to check the detection information of the molecule to be detected 2 with the existing reference information, the information receiving unit 42 obtains the reference information over the network. The information checking unit 43 checks the obtained reference information with the detection information. Information is obtained from an external network to be referred to, and thereby a function of carrying a lot of information and analyzing them can be replaced with an alternative externally. Consequently, further miniaturization of the molecular detection apparatus 1 is enabled to increase the portability. Further, using a network transmitting means also makes it possible to obtain new signal patterns by the pattern recognition method immediately. On the information receiving side, it is possible to make a next action based on this information. It is possible to use the molecular detection apparatus 1 in such a way that the portable molecular detection apparatus 1 is disposed at respective places and data to be obtained are collected from the respective places to be analyzed, and then the analyzed data are utilized for evacuation guidance under abnormal circumstances or the like. The network and the molecular detection apparatus 1 are combined, and thereby a lot of use ways, which were not able to be achieved conventionally, are created and its industrial value improves.

Next, specific examples and evaluation results thereof will be described.

EXAMPLE 1

First, a detection element in which a GEFT and an organic probe are combined is prepared as follows. A graphene layer is formed by transferring graphite onto a substrate by an exfoliation method or by depositing graphene on a metal surface by means of a chemical vapor deposition method (CVD). A single layer or plural layers of graphene deposited on the metal surface is/are transferred onto a polymer film, and the resultant is transferred again onto a desired semiconductor substrate for field effect transistor (FET) fabrication. For example, graphene is formed on a surface of a copper foil by CVD with flowing of a methane gas under the condition of about 1000° C.

Next, a polymethyl methacrylate film is applied at 4000 rpm by a spin coating method, and the opposite surface of the copper foil film is etched with an ammonium persulfate solution of 0.1 M, and thereby a graphene film floating in the solution is recovered. By doing this, the graphene film is transferred onto the polymethyl methacrylate film side. A surface of the graphene film is sufficiently cleaned, and then this is transferred onto a silicon substrate again. The redundant polymethyl methacrylate film is dissolved with acetone to be removed. A resist is applied onto the graphene transferred onto the silicon substrate to undergo patterning, and a pattern with a 10-μm electrode interval is formed by oxygen plasma. Electrodes are deposited to form an FET structure on which a source electrode and a drain electrode are provided. The graphene is disposed on an oxide film formed on the surface of the silicon substrate and an FET type sensor structure is formed in which the graphene is sandwiched between the source electrode and the drain electrode and the silicon substrate side is set as the gate electrode.

Next, an organic probe is provided on the surface of the graphene. The organic probe is installed in a manner that an organic compound is dissolved in a methanol solution with a concentration of 10 nM and a graphene sensor surface is immersed in the resultant solution for several minutes. For the organic probe, the organic compounds 2A, 2C, and 3 illustrated in FIG. 8 and the organic compound 1A illustrated in FIG. 7 are used. In Example, 1, as illustrated in FIG. 5, the four detection cells A to D are provided on a detection surface of a detector, and the organic compound 2A is installed at the detection cell A, the organic compound 2C is installed at the detection cell B, the organic compound 1A is installed at the detection cell C, and the organic compound 3 is installed at the detection cell D respectively as the organic probe. As described previously, the organic compounds 1A, 2A, 2C, and 3 are respectively different in the bond strength with the molecule to be detected (nitro compound).

Next, a molecule to be detected 1 (2,4,6-trinitrotoluene), a molecule to be detected 2 (2,4-dinitrotoluene), and a molecule to be detected 3 (2,3-dimethyl-2,3-dinitrobutane) that are illustrated in FIG. 10 are prepared. A vapor of the molecule to be detected 1 is diluted with a nitrogen gas to be about 5 ppb in concentration and a dilute gas is sent to the detector. The molecule to be detected 1 is captured by each of the organic probes in the detection cells A to D. Since the organic probes in the detection cells A to D are respectively different in the bond strength with the molecule to be detected, signals to be detected by the gate electrodes are also different respectively. Results of detection by the detection cells A to D are sent to a discriminator that processes signals, and are converted into intensities. The detection results are output as a relative intensity display as illustrated in FIG. 6. Signal intensities of the detection cells, which are the detection results of the molecule to be detected 1, are illustrated in Table 1.

TABLE 1

| Detection Cell | Organic Probe Disposed In Detection Cell | Detection Intensity |
| --- | --- | --- |
| A | Organic Compound 2A | 3 |
| B | Organic Compound 2C | 5 |
| C | Organic Compound 1A | 1 |
| D | Organic Compound 3 | 0 |

In the detection results of Table 1, the intensity of the detection signal of the detection cell D is lower by two digits or more as compared to the other detection cells, and thus is described as "0." Table 1 reveals that as for the detection results of the molecule to be detected 1, signal patterns based on differences of the signal intensities of the detection cells A to D are exhibited and based on such signal patterns, the molecule to be detected 1 is discriminated, thereby enabling selective and higher sensitive detection of the molecule to be detected 1 having an extremely low concentration in the order of ppb.

Similarly, a vapor of the molecule to be detected 2 is diluted with a nitrogen gas to be about 20 ppb in concentration, to then be sent to the detector. Detection results of the molecule to be detected 2 are illustrated in Table 2. Table 2 reveals that as for the detection results of the molecule to be detected 2, signal patterns based on differences of the signal intensities of the detection cells A to D are exhibited and based on such signal patterns, the molecule to be detected 2 is discriminated, thereby enabling selective and higher sensitive detection of the molecule to be detected 2 having an extremely low concentration in the order of ppb.

TABLE 2

| Detection Cell | Organic Probe Disposed In Detection Cell | Detection Intensity |
| --- | --- | --- |
| A | Organic Compound 2A | 2 |
| B | Organic Compound 2C | 4 |
| C | Organic Compound 1A | 1 |
| D | Organic Compound 3 | 0 |

Further similarly, a vapor of the molecule to be detected 3 is diluted with a nitrogen gas to be about 20 ppb in concentration, to then be sent to the detector. Detection results of the molecule to be detected 3 are illustrated in Table 3. Table 3 reveals that as for the detection results of the molecule to be detected 3, signal patterns based on differences of the signal intensities of the detection cells A to D are exhibited and based on such signal patterns, the molecule to be detected 3 is discriminated, thereby enabling selective and higher sensitive detection of the molecule to be detected 3 having an extremely low concentration in the order of ppb.

TABLE 3

| Detection Cell | Organic Probe Disposed In Detection Cell | Detection Intensity |
| --- | --- | --- |
| A | Organic Compound 2A | 4 |
| B | Organic Compound 2C | 5 |
| C | Organic Compound 1A | 2 |
| D | Organic Compound 3 | 0 |

EXAMPLE 2

A detector is formed in the same manner as in Example 1 except that the organic compounds 2B, 2D, and 3 that are illustrated in FIG. 8 and the organic compound 1A illustrated in FIG. 7 are used as the organic probe provided on the surface of the graphene of the GFET sensor fabricated in the same manner as in Example 1. By using such a detector, the molecule to be detected 1 (2,4,6-trinitrotoluene) illustrated in FIG. 10 is detected. That is, a vapor of the molecule to be detected 1 is diluted with a nitrogen gas to be about 5 ppb in concentration, to then be sent to the detector. Detection results of the molecule to be detected 1 are illustrated in Table 4. Table 4 reveals that as for the detection results of the molecule to be detected 1, signal patterns based on differences of the signal intensities of the detection cells A to D are exhibited and based on such signal patterns, the molecule to be detected 1 is discriminated, thereby enabling selective and higher sensitive detection of the molecule to be detected 1 having an extremely low concentration in the order of ppb.

TABLE 4

| Detection Cell | Organic Probe Disposed In Detection Cell | Detection Intensity |
| --- | --- | --- |
| A | Organic Compound 2B | 2 |
| B | Organic Compound 2D | 3 |
| C | Organic Compound 1A | 1 |
| D | Organic Compound 3 | 0 |

While certain embodiments have been described, these embodiments have been presented by way of example only, and are not intended to limit the scope of the inventions.

Indeed, the novel embodiments described herein may be embodied in a variety of other forms; furthermore, various omissions, substitutions and changes in the form of the embodiments described herein may be made without departing from the spirit of the inventions. The inventions described in the accompanying claims and their equivalents are intended to cover such forms or modifications as would fall within the scope and spirit of the inventions.

What is claimed is:

1. A molecular detection apparatus, comprising:
a detector including a detection cell having a sensor unit and an organic probe disposed at the sensor unit and capturing a molecule to be detected,
wherein the sensor unit comprises a field effect transistor including a graphene layer, and a source electrode and a drain electrode both connected to the graphene layer,
the organic probe is provided on the graphene layer, and is comprised of an organic compound including a head portion having an aromatic hydrocarbon group containing a phosphonate group which has a hydroxy group as a reactive group with respect to the molecule or a phosphate group which has a hydroxy group as a reactive group with respect to the molecule, a base portion having a polycyclic aromatic hydrocarbon group, and a connecting portion having a single bond or an organic group connecting the head portion and the base portion, and
the organic compound comprises at least one selected from the group consisting of the following compound (2A), compound (2B), compound (2C), and compound (2D):

[compound 2A]
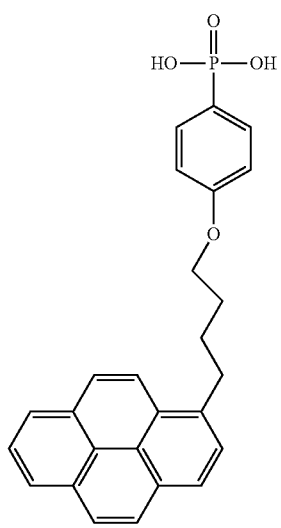

[compound 2B]
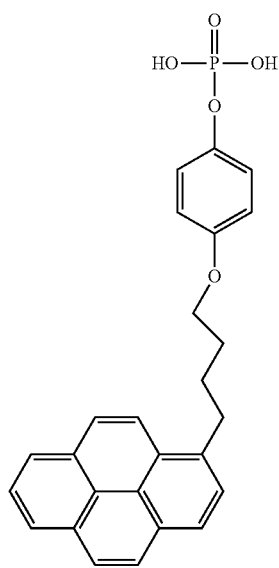

[compound 2C]
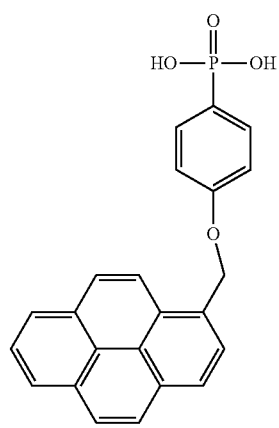

[compound 2D]
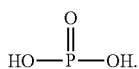

2. The molecular detection apparatus of claim 1, wherein the detector includes a plurality of the detection cells having a plurality of the sensor units, a first organic probe same as the organic probe, and a second organic probe different from the organic probe, the first organic probe being provided on at least one of the plurality of the sensor units, and the second organic probe being provided on an other one of the plurality of the sensor units.

3. The molecular detection apparatus of claim 2, wherein a plurality of organic probes containing the first and second organic probes are different in bond strength with the molecule to be detected.

4. The molecular detection apparatus of claim 1, wherein the molecule to be detected contains a nitro compound molecule.

5. A molecular detector, comprising:
a sensor unit including a field effect transistor having a graphene layer and a source electrode and a drain electrode both connected to the graphene layer; and
an organic probe provided at the graphene layer of the sensor unit and which is comprised of an organic compound including a head portion having an aromatic hydrocarbon group containing a phosphonate group which has a hydroxy group as a reactive group or a phosphate group which has a hydroxy group as a reactive group with respect to a molecule to be detected, a base portion having a polycyclic aromatic hydrocarbon group, and a connecting portion having a single bond or an organic group connecting the head portion and the base portion,
wherein the organic compound comprises at least one selected from the group consisting of the following compound (2A), compound (2B), compound (2C), and compound (2D):

[compound 2A]

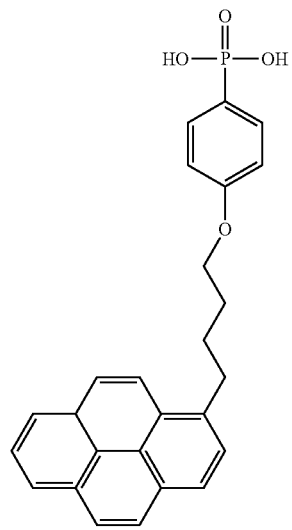

[compound 2B]

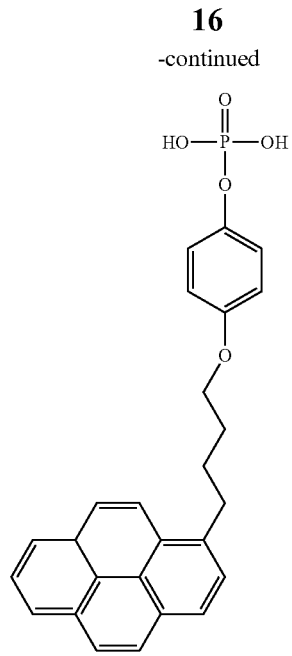

[compound 2C]

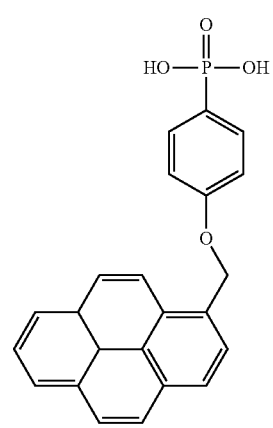

[compound 2D]

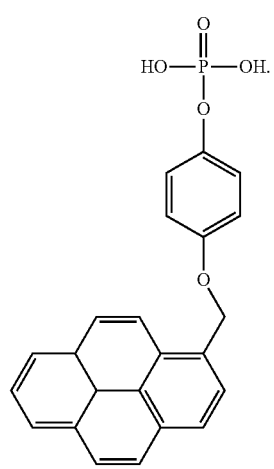

6. The molecular detection apparatus according to claim 1, further comprising:
a collection unit configured to collect detection target gas containing the molecule to be detected.

7. The molecular detection apparatus according to claim 1, further comprising:
a discriminator configured to discriminate the molecule to be detected by a detection signal generated from the sensor unit by the molecule being captured by the organic probe in the detection cell.

\* \* \* \* \*